(12) United States Patent
Oh et al.

(10) Patent No.: US 11,882,392 B2
(45) Date of Patent: Jan. 23, 2024

(54) SOUND OUTPUT DEVICE

(71) Applicant: IRTRONIX, INC., Torrance, CA (US)

(72) Inventors: Danny Oh, Torrance, CA (US); Chien Nguyen, Santa Ana, CA (US)

(73) Assignee: IRTRONIX, INC., Torrance, CA (US)

( * ) Notice: Subject to any disclaimer, the term of this patent is extended or adjusted under 35 U.S.C. 154(b) by 178 days.

(21) Appl. No.: 17/423,842

(22) PCT Filed: Jan. 17, 2020

(86) PCT No.: PCT/KR2020/000883
§ 371 (c)(1),
(2) Date: Jul. 16, 2021

(87) PCT Pub. No.: WO2020/149707
PCT Pub. Date: Jul. 23, 2020

(65) Prior Publication Data
US 2022/0086547 A1    Mar. 17, 2022

Related U.S. Application Data

(60) Provisional application No. 62/794,237, filed on Jan. 18, 2019.

(51) Int. Cl.
| | |
|---|---|
| *H04R 1/02* | (2006.01) |
| *H04R 1/10* | (2006.01) |
| *F24F 8/22* | (2021.01) |
| *A61L 2/10* | (2006.01) |
| *F21Y 115/10* | (2016.01) |

(52) U.S. Cl.
CPC ............... *H04R 1/028* (2013.01); *A61L 2/10* (2013.01); *F24F 8/22* (2021.01); *H04R 1/025* (2013.01); *H04R 1/1016* (2013.01); *A61L 2202/14* (2013.01); *F21Y 2115/10* (2016.08)

(58) Field of Classification Search
CPC ...... H04R 1/028; H04R 1/025; H04R 1/1016; F24F 8/22; A61L 2/10; A61L 2202/14; F21Y 2115/10
USPC .......................................................... 381/380
See application file for complete search history.

(56) References Cited

U.S. PATENT DOCUMENTS

| | | | |
|---|---|---|---|
| 2013/0131519 A1* | 5/2013 | LeBoeuf | ............... A61B 5/681 600/476 |
| 2018/0098144 A1 | 4/2018 | Thoen | |
| 2018/0332379 A1 | 11/2018 | McGarry et al. | |

FOREIGN PATENT DOCUMENTS

| | | |
|---|---|---|
| JP | 2010-094152 A | 4/2010 |
| JP | 2016-163770 A | 9/2016 |
| JP | 2018-108467 A | 7/2018 |
| KR | 10-1122751 B1 | 3/2012 |
| KR | 10-2015-0105016 A | 9/2015 |

(Continued)

*Primary Examiner* — Sean H Nguyen
(74) *Attorney, Agent, or Firm* — Heedong Chae; Lucem, PC

(57) ABSTRACT

A sound output device according to an exemplary embodiment of the present invention includes: a first housing; a second housing; a substrate; a light emitting unit; and a sound output unit, in which the second housing is connected with the first housing, the substrate is disposed inside the first housing or the second housing, the sound output unit is connected with the substrate, the light emitting unit is connected with the substrate, and the second housing selectively transmits light emitted by the light emitting unit based on a wavelength thereof.

12 Claims, 8 Drawing Sheets

(56) References Cited

FOREIGN PATENT DOCUMENTS

KR 10-1912166 B1 10/2018
KR 10-2018-0130831 A 12/2018

* cited by examiner

SOUND OUTPUT DEVICE

TECHNICAL FIELD

The present technology relates to a sound output device, and more particularly, to a sound output device having a light emitting function.

BACKGROUND ART

An earphone is an abbreviation of an earphone receiver, and is a device implemented such that a user listens to various sounds output from a portable cassette player, an MP3 player, other sound generating terminals, and the like without disturbing others, and has a shape that is inserted into the user's ear hole for portability and smooth sound output. The earphone may be exposed to various contaminant environments. In particular, the earphone is continuously used in many cases without a separate washing or sterilization process, but various germs or viruses may penetrate through the ear hole, which may cause a problem for hygiene.

In the meantime, otitis media caused by infection with bacteria or viruses in the middle ear inside the ear is caused by various causes, such as a cold, allergies, and family medical history, and an exudate becomes a purulent to increase pressure, and bursts the eardrum, and flows out into the ear canal. As described above, when a hole is formed in the eardrum and a purulent secretion flows out, the exudate discharged through the ruptured eardrum is hardened. If the ruptured eardrum is not regenerated due to this reason, a difficulty in hearing occurs. Accordingly, there is a need for a treatment method through a familiar device, such as an earphone.

DISCLOSURE

Technical Problem

An object of a technical spirit according to exemplary embodiments of the present invention is to provide a sound output device having a sterilization and/or otitis media treatment function through irradiation of light in a specific wavelength band.

Technical Solution

A sound output device according to an exemplary embodiment of the present invention includes: a first housing; a second housing; a substrate; a light emitting unit; and a sound output unit, in which the second housing is connected with the first housing, the substrate is disposed inside the first housing or the second housing, the sound output unit is connected with the substrate, the light emitting unit is connected with the substrate, and the second housing selectively transmit light emitted by the light emitting unit based on a wavelength thereof.

In the exemplary embodiment, the second housing may selectively transmit the light emitted by the light emitting unit through an entire area or a partial area thereof.

In the exemplary embodiment, the partial areas may be continuously or discontinuously distributed on the second housing.

In the exemplary embodiment, the partial areas may be discontinuously distributed in a direction of more than 0° and less than 180° based on an output direction of the sound signal output from the sound output unit.

In the exemplary embodiment, the second housing may protrude in one direction of the first housing, and include a first area and a second area formed on an outer circumferential surface thereof in the one direction and having different light transmission characteristics.

In the exemplary embodiment, the first area and the second area may be formed in a lattice form on an outer circumferential surface of the second housing.

In the exemplary embodiment, the first area may be formed on an inner portion of an outer circumferential surface of the second housing, and the second area may be formed on an outer portion of an outer circumferential surface of the second housing.

In the exemplary embodiment, the first area may be made of a material having higher UVA transmissivity than UVA transmissivity of the second area.

In the exemplary embodiment, the first area may be made of a material having higher UVC transmissivity than the second area.

In the exemplary embodiment, the first area may be made of a material having higher infrared transmissivity than infrared transmissivity of the second area.

In the exemplary embodiment, the light emitting unit may include at least one light source configured to emit at least any one of UVA, UVB, UVC, and infrared rays.

In the exemplary embodiment, the sound output device may further include a control unit disposed on the substrate and configured to control an operation of at least one of the light emitting unit and the sound output unit, in which the control unit may drive the light emitting unit for a predetermined time when a sound signal is received from a terminal.

In the exemplary embodiment, the sound output unit may amplify a sound collected from the outside and output the amplified sound.

Advantageous Effects

The sound output device according to the exemplary embodiment of the present invention may have a sterilization and/or otitis media treatment function through irradiation of light in a specific wavelength band.

The sound output device according to the exemplary embodiment of the present invention may reduce heat generation of the light source by controlling the light to be irradiated for a predetermined time.

BEST MODE

A sound output device according to an exemplary embodiment of the present invention includes: a first housing; a second housing; a substrate; a light emitting unit; and a sound output unit, in which the second housing is connected with the first housing, the substrate is disposed inside the first housing or the second housing, the sound output unit is connected with the substrate, the light emitting unit is connected with the substrate, and the second housing selectively transmits light emitted by the light emitting unit based on a wavelength thereof.

MODE FOR CARRYING OUT THE INVENTION

Hereinafter, multiple various exemplary embodiments or examples in which various characteristics of the present invention are implemented are provided. A specific example and arrangement of a device are described to simply represent the present invention. The specific example and arrangement are only examples and are not interpreted to have a limited meaning. Further, reference numbers of the drawings and/or letters are repeatedly used in various examples of the present invention.

Such repetition is used for the purpose of simplification and clarification, and does not specify the relationship between various exemplary embodiments and/or discussed configurations.

Further, in the entire specification, when a part "includes" a certain constituent element, it means that other constituent elements may be further included, rather than excluding other constituent elements, unless explicitly described to the contrary, and phrases such as a specific constituent element is "on anther constituent element", "is connected to . . . ", and/or "is coupled to . . . " may include an exemplary embodiment in which two constituent elements are directly connected, and may also include an exemplary embodiment in which another constituent element is additionally disposed between the two constituent elements, so that the two constituent elements are not directly connected.

Unless defined otherwise, all of the terminologies used herein and containing technical or scientific terminologies have the same meanings as those generally understood by a person skilled in the art to which the present invention pertains. Terms defined in generally used dictionaries shall be construed to have a meaning equal to that in the context of a related technology, and shall not be construed as ideal or excessively formal meanings, unless clearly defined in the present specification.

Figure 1:
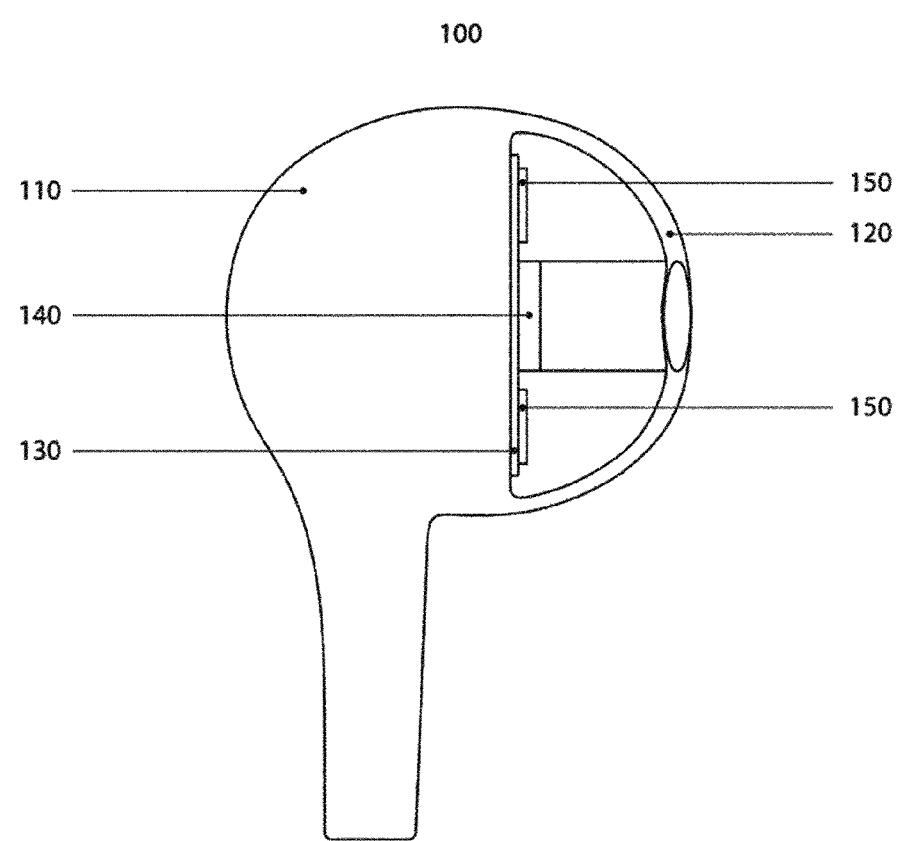
FIG. 1 is a lateral view illustrating a sound output device according to an exemplary embodiment of the present invention.

FIG. 1 is a lateral view illustrating a sound output device according to an exemplary embodiment of the present invention.

Referring to FIG. 1, a sound output device 100 according to an exemplary embodiment of the present invention may include a first housing 110, a second housing 120, a substrate 130, a sound output unit 140, and a light emitting unit 150.

The first housing 110 may be coupled to the second housing 120. The second housing 120 may be coupled with the first housing 110 so as to protrude in one direction of the first housing 110, but the present invention is not limited thereto, and the second housing 120 may be coupled with the first housing 110 in various forms.

For example, the second housing 120 may have a convex form so as to be easily inserted into an ear hole of a user, and may be coupled with the first housing 110 so as to protrude in one direction of the first housing 110. The first housing 110 may be coupled with the second housing 120 to form an internal space, and the substrate 130, the sound output unit 140, and the light emitting unit 150 may be disposed in the formed internal space.

The first housing 110 may be made of a material having light transmittance or a material having no light transmittance. For example, the first housing 110 may be made of an opaque plastic material, but the material thereof is not limited thereto. In the meantime, at least one hole for a microphone (not illustrated) used for a noise cancelling function or a hearing aid function may be formed in a surface of the first housing 110.

The second housing 120 may transmit light emitted by the light emitting unit 150. To this end, the second housing 120 may be made of a material having light transmittance. Further, the second housing 120 may selectively transmit light emitted by the light emitting unit 150 based on a wavelength thereof. An entire area or a partial area of the second housing 120 may be made of a material having light transmittance. The partial areas may be continuously or discontinuously distributed on the second housing 120. Accordingly, the light emitted by the light emitting unit 150 may selectively pass through the second housing 120 according to the material of the entire area, the distribution form of the partial areas, and/or the materials of the partial area.

The substrate 130 may be disposed inside the first housing 110 or the second housing 120. The sound output unit 140 and the light emitting unit 150 may be disposed on the substrate 130, and various configurations, such as a control unit, a communication unit, and a battery, which are to be described below, may be disposed thereon.

The sound output unit 140 may output a sound signal. The sound output unit 140 may be connected with the substrate 130. The sound signal output from a distal end of the sound output unit 140 may be transferred to the ear of the user.

The light emitting unit 150 may emit light. The light emitting unit 150 may be connected with the substrate 130. The light emitting unit 150 may include at least one light source emitting at least one of UVA, UVB, UVC, and infrared rays. Herein, UVA may be defined as ultraviolet rays in a wavelength band of about 400 to 315 nm, UVB may be defined as ultraviolet rays in a wavelength band of about 315 to 280 nm, and UVC may be defined as ultraviolet rays in a wavelength band of about 280 to 100 nm.

For example, according to the exemplary embodiment, the light emitting unit 150 includes a light emitting diode, but is not limited thereto. The light emitting diode may be used in various display devices, backlight light sources, lighting devices, and the like based on advantages, such as low power consumption, high lifespan, and eco-friendliness, and may emit various ranges of wavelengths, such as IR, UVA, UVB, and UVC. For example, the wavelength band may vary in the range from 100 nm to 1,000 nm.

As described above, the second housing 120 may selectively transmit the light emitted by the light emitting unit 150 based on the wavelength thereof. Further, the second housing 120 may selectively transmit the light emitted by the light emitting unit 150 through the entire area or the partial area thereof.

For example, the second housing 120 may selectively transmit only UVA through the entire area thereof, and the UVA having passed therethrough is emitted to the ear of the user to provide antibacterial and sterilizing effects. Further, the second housing 120 may selectively transmit UVA through the partial area thereof, and also selectively transmit UVC through the partial area thereof. This will be described below in more detail.

Figure 2:
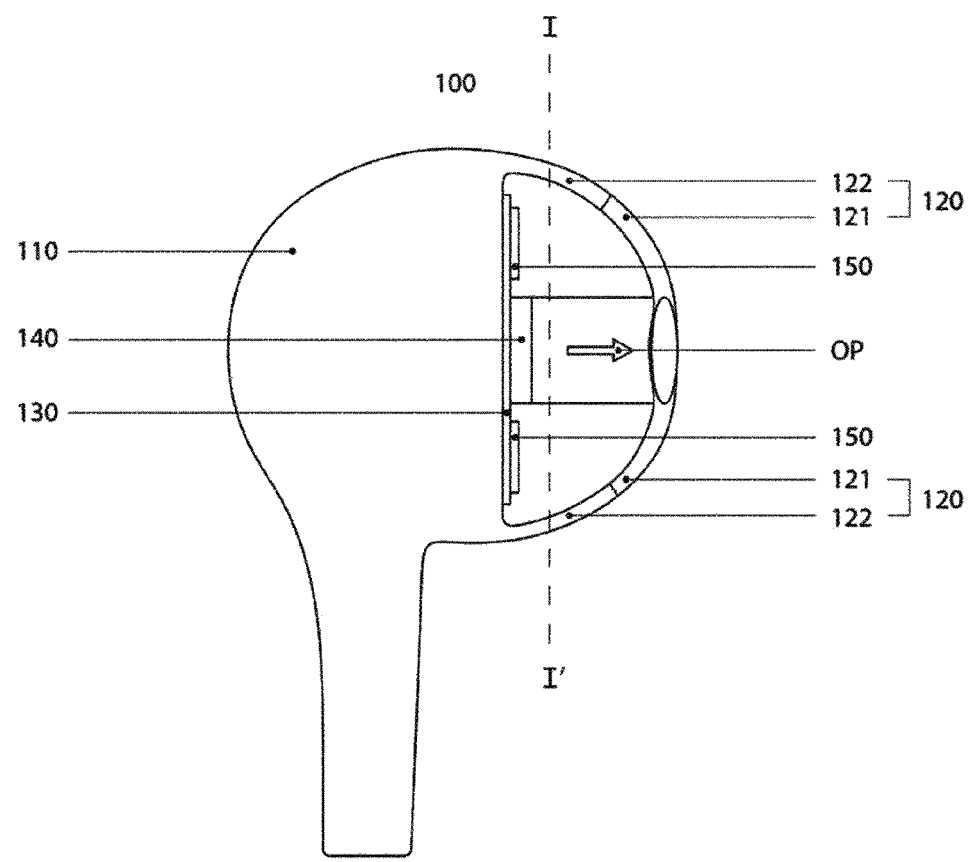
FIG. 2 is a diagram concretely illustrating the lateral view of the sound output device according to the exemplary embodiment of the present invention.
Figure 3:
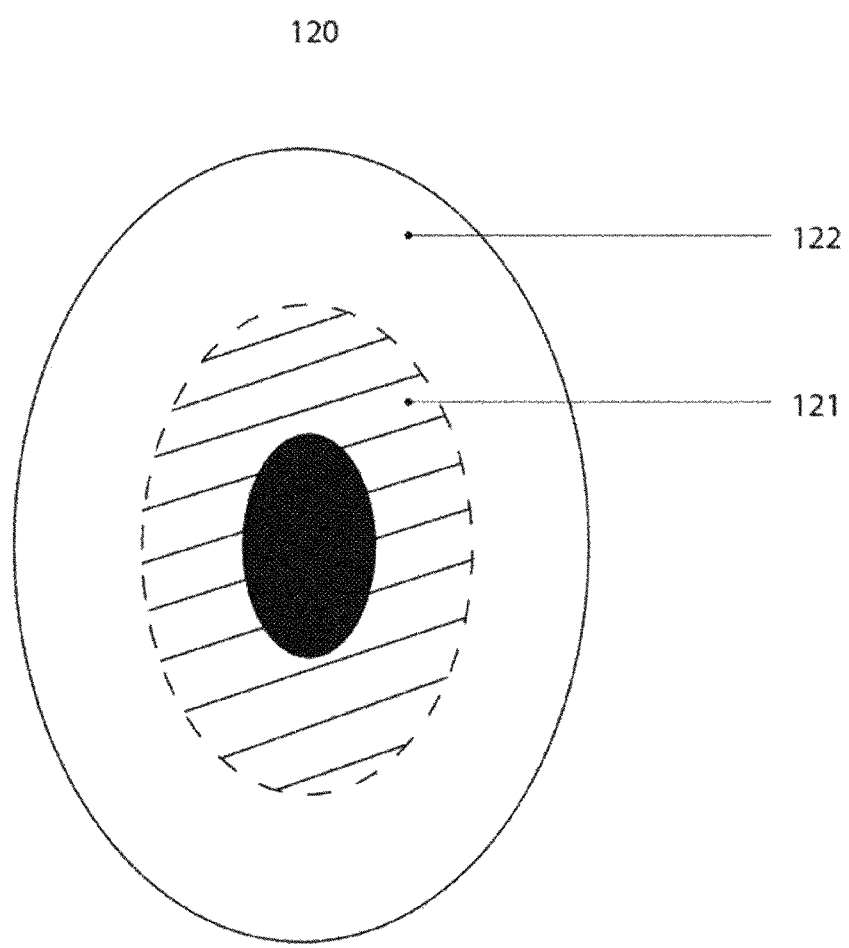
FIGS. 3 to 5 are diagrams illustrating a front surface of a second housing of the sound output device according to exemplary embodiments of the present invention.
Figure 4:
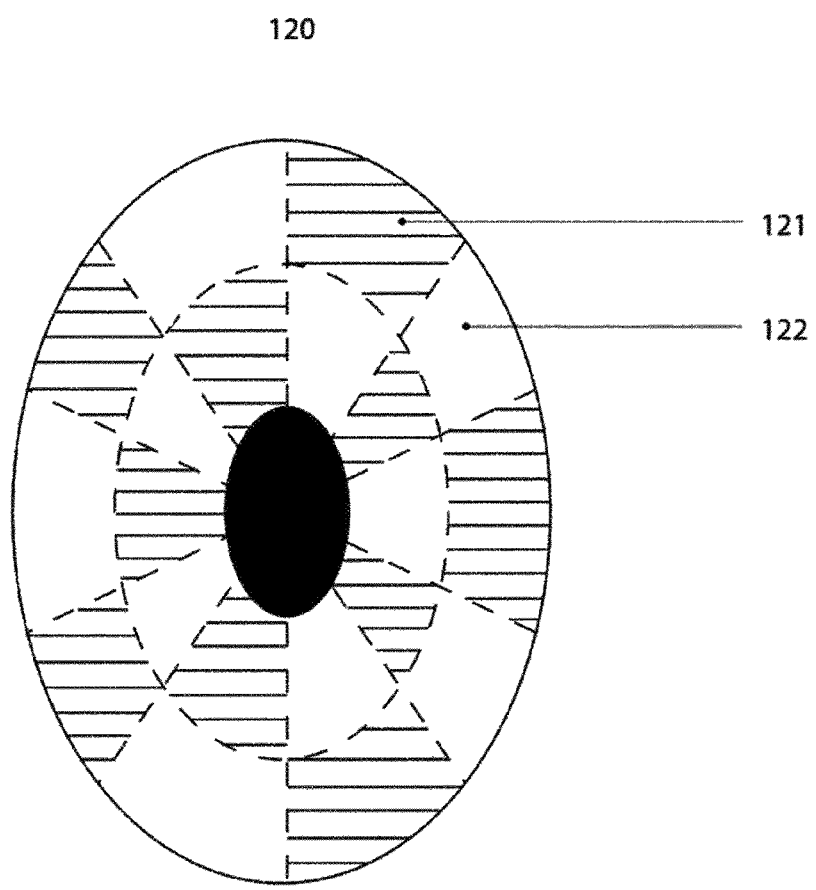
Figure 5:
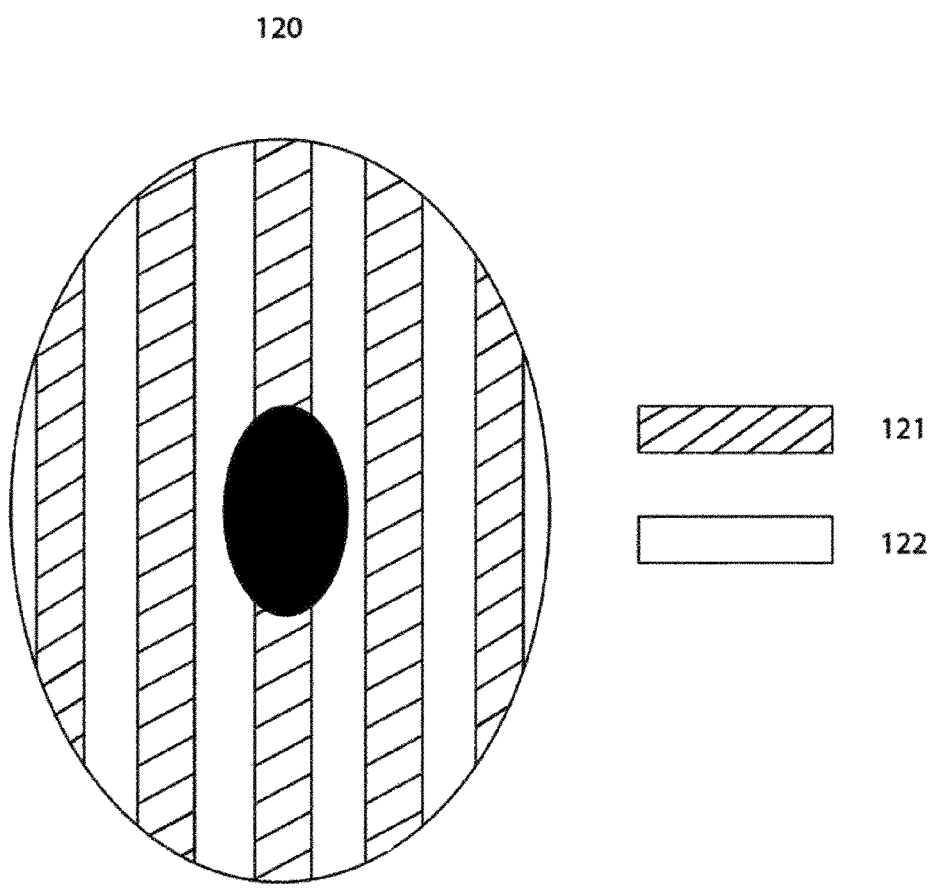
Figure 6:
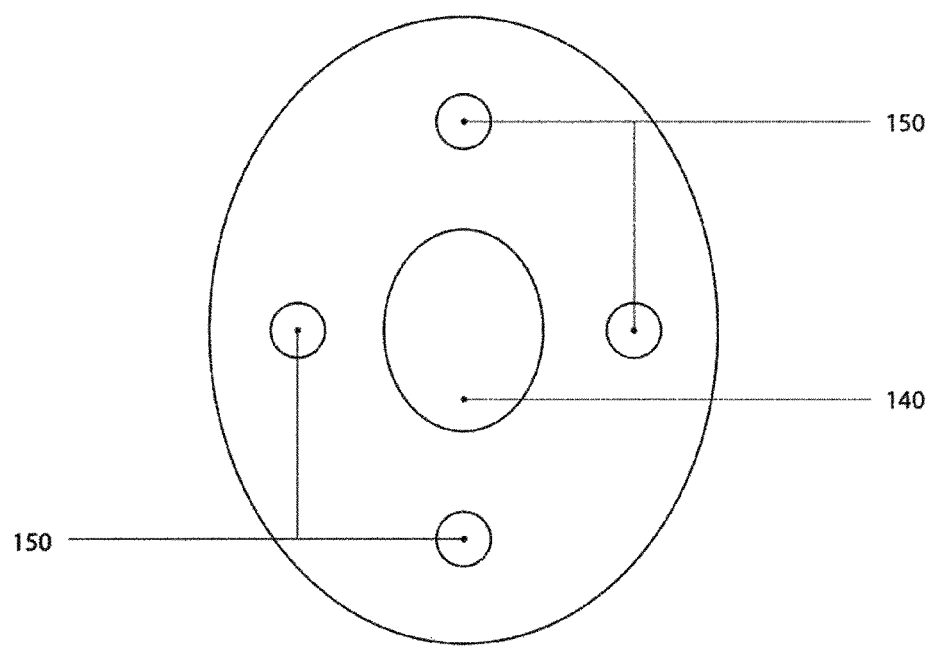
FIG. 6 is a cross-sectional view illustrating a cross-section taken along an axis I-I' of FIG. 2.

FIG. 2 is a diagram concretely illustrating the lateral view of the sound output device according to the exemplary embodiment of the present invention. FIGS. 3 to 5 are diagrams illustrating a front surface of the second housing of the sound output device according to the exemplary embodiment of the present invention. FIG. 6 is a cross-sectional view illustrating a cross-section taken along an axis I-I' of FIG. 2.

First, referring to FIG. 2, the sound output device 100 according to the exemplary embodiment of the present invention may include the first housing 110, the second housing 120, the substrate 130, the sound output unit 140, and the light emitting unit 150.

The second housing 120 may include a first area 121 and a second area 122. At least one of the first area 121 and the second area 122 may transmit light emitted by the light emitting unit 150. FIG. 2 illustrates that the first area 121 is formed on an inner portion of an outer circumferential surface of the second housing 120 and the second area 122 is formed on an outer portion of the outer circumferential surface of the second housing 120, but the present invention is not limited thereto, and the first area 121 and the second area 122 may be formed or distributed in various forms.

For example, when the first area 121 may transmit the light emitted by the light emitting unit 150 and the second area 122 does not transmit the light emitted by the light emitting unit 150, the first areas 121 may be continuously or discontinuously distributed on the second housing 120. Further, for example, the first areas 121 may be discontinuously distributed in a direction greater than 0° and less than 180° based on an output direction OP of the sound signal output from the sound output unit 140.

The first area 121 and the second area 122 may be made of the same material, and may be made of different materials.

For example, both the first area 121 and the second area 122 may be made of a material that transmits UVA, UVB, UVC, or infrared rays. Further, for example, the first area 121 may be made of a material that transmits UVA, UVB, UVC, or infrared rays, and the second area 122 may be made of a material that does not transmit light. Further, for example, the first area 121 may be made of a material that transmits UVA, UVB, UVC, or infrared rays, and the second area 122 may be made of a material that transmits any one of lights, which the first area 121 does not transmit.

Referring to FIGS. 3 to 5, various forms of the first area 121 and the second area 122 are illustrated. First, as illustrated in FIG. 3, the first area 121 may be formed on the inner portion of the outer circumferential surface of the second housing 120 and the second area 122 may be formed on the outer portion of the outer circumferential surface of the second housing 120.

For example, the first area 121 may be made of a material that transmits UVA, UVB, UVC, or infrared rays, and the second area 122 may be made of a material that does not transmit light. Further, for example, the first area 121 may be made of a material that transmits UVC, and the second area 122 may also be made of a material that transmits UVA. In this case, UVC may be emitted into the ear hole to induce sterilization/antibacterial effect of air, and UVA may be emitted toward the auricle to induce sterilization/antibacterial effect of skin.

Referring to FIG. 4, the first area 121 and the second area 122 may also be formed in a lattice form on the outer circumferential surface of the second housing 120. For example, the first area 121 may be made of a material having higher UVA transmissivity, higher UVC transmissivity, or higher infrared transmissivity than the second area 122, but the material thereof is not limited thereto.

Referring to FIG. 5, the first area 121 and the second area 122 may be alternately formed. For example, the first area 121 may be made of a material that transmits UVA, UVB, UVC, or infrared rays, and the second area 122 may be made of a material that does not transmit light. Further, for example, the first area 121 may be made of a material that transmits UVC, and the second area 122 may also be made of a material that transmits UVA.

In the meantime, referring to FIG. 6, at least one light emitting unit 150 may be disposed along a circumference of the sound output unit 140, and FIG. 3 illustrates that the number of the light emitting units 150 is four, but the present invention is not limited thereto, and the number and locations of the light emitting units 150 may be variously changed according to a design.

Figure 7:
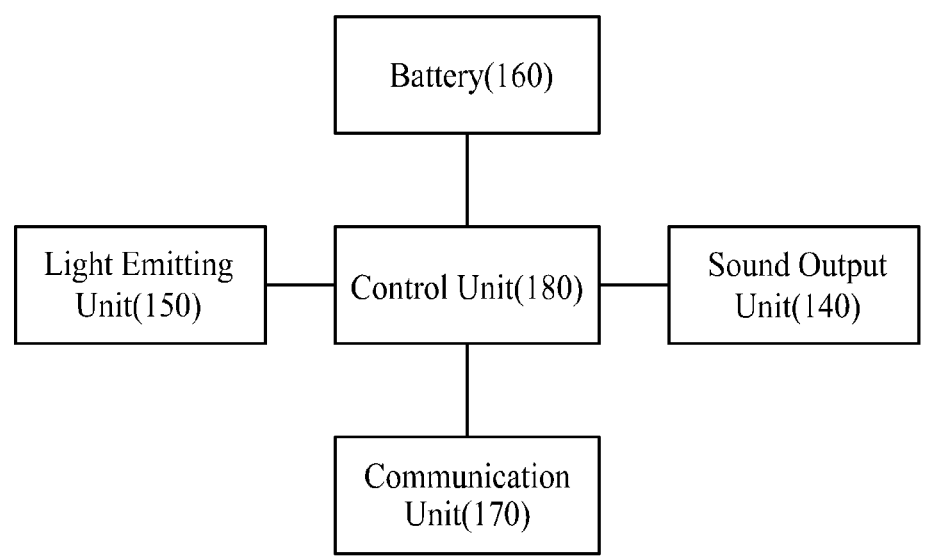
FIG. 7 is a block diagram illustrating the sound output device according to the exemplary embodiment of the present invention.

FIG. 7 is a block diagram illustrating the sound output device according to the exemplary embodiment of the present invention.

Referring to FIG. 7, the sound output device 100 according to the exemplary embodiment of the present invention may include a battery 160, a communication unit 170, and a control unit 180 in addition to the first housing 110, the second housing 120, the substrate 130, the sound output unit 140, and the light emitting unit 150.

The battery 160 may supply power to the sound output device 100. The battery 160 may be charged with power supplied from the outside under the control of the control unit 180.

The communication unit 170 may receive various signals and/or control commands from a terminal. For example, the communication unit 170 may receive a sound signal from the terminal. The communication unit 170 may include a Bluetooth module, but is not limited thereto, and may include various types of communication modules.

The control unit 180 may control the overall operation of the sound output device 100. For example, the control unit 180 may control the operation of the sound output device 100 based on a control command transmitted from the terminal through the communication unit 170. The control unit 180 may control the light emitting unit 150 to emit light for a predetermined time when a sound signal is received. Accordingly, it is possible to suppress excessive heat generation in the light emitting unit 150 by controlling the emission time of the light emitting unit 150.

Figure 8:
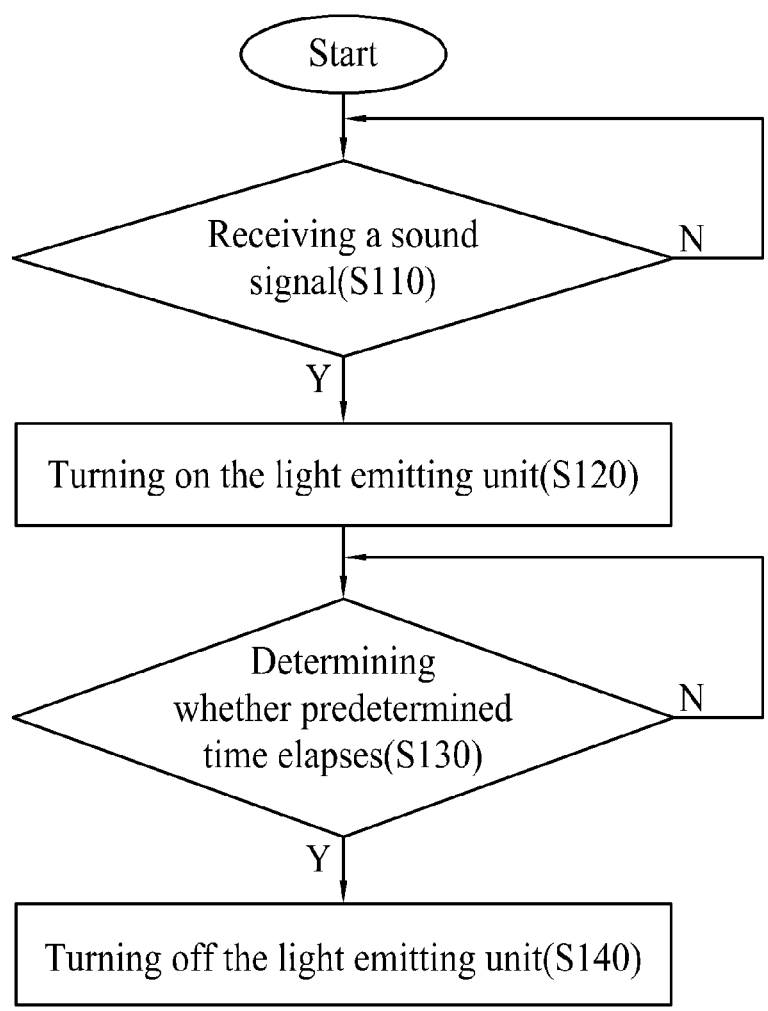
FIG. 8 is a flowchart illustrating an operating method of a sound output device according to an exemplary embodiment of the present invention.

FIG. 8 is a flowchart illustrating an operating method of the sound output device according to the exemplary embodiment of the present invention.

Referring to FIG. 8, the operating method of the sound output device according to the exemplary embodiment of the present invention may include: receiving a sound signal (S110), turning on the light emitting unit (S120), determining whether a predetermined time elapses (S130), and turning off the light emitting unit based on the determination result (S140).

Hereinafter, operations S110, S120, S130, and S140 will be described with reference to FIG. 8.

In operation S110, the control unit 180 may receive a sound signal. For example, the control unit 180 may receive a sound signal from an external terminal through the communication unit 170.

In operation S120, the control unit 180 may turn on the light emitting unit 150.

In operation S130, the control unit 180 may determine whether a predetermined time elapses. Herein, the predetermined time may also be set through a terminal by a user, and may also be determined by the control unit 180 based on a reproduction length of the sound signal.

In operation S140, the control unit 180 may turn off the light emitting unit 150 when the predetermined time elapses.

The sound output device 100 according to the exemplary embodiments of the present invention may be applied to various devices, such as an earphone, an ear set, and/or a hearing aid. When the sound output device 100 according to the exemplary embodiments of the present invention is implemented in a hearing aid, the sound output device 100 may be carried output such that the light emitting unit 150 radiates UVA, UVB, UVC, and/or infrared rays while the sound output unit 150 and/or the control unit 180 amplifies and output the sound signal collected through a microphone.

As described above, the present invention has been described with reference to the specific matters, such as a specific component, limited embodiments, and drawings, but these are provided only for helping general understanding of the present invention, and the present invention is not limited to the aforementioned exemplary embodiments, and those skilled in the art will appreciate that various changes and modifications are possible from the description.

Accordingly, the spirit of the present invention shall not be determined while being limited to the foregoing exemplary embodiments, and it will be considered that all matters having equivalent or equivalent modifications to the claims are within the scope of the present invention.

INDUSTRIAL APPLICABILITY

The present technology relates to a sound output device, and more particularly, to a sound output device having a light emitting function.

The invention claimed is:

1. A sound output device, comprising:
   a first housing;
   a second housing;
   a substrate;
   a light emitting unit; and
   a sound output unit,
   wherein the second housing is connected with the first housing,
   the substrate is disposed inside the first housing or the second housing,
   the sound output unit is connected with the substrate,
   the light emitting unit is connected with the substrate,
   the second housing selectively transmits light emitted by the light emitting unit based on a wavelength thereof, and wherein the second housing protrudes in one direction of the first housing, and includes a first area and a second area formed on an outer circumferential surface thereof in the one direction and having different light transmission characteristics.

2. The sound output device of claim 1, wherein the second housing selectively transmits the light emitted by the light emitting unit through at least one of the first area, the second area, and an entire area including the first area and the second area.

3. The sound output device of claim 2, wherein the first area and the second area are continuously or discontinuously distributed on the second housing.

4. The sound output device of claim 1, wherein the first area and the second area are discontinuously distributed in a direction of more than 0° and less than 180° based on an output direction of the sound signal output from the sound output unit.

5. The sound output device of claim 1, wherein the first area and the second area are formed in a lattice form on an outer circumferential surface of the second housing.

6. The sound output device of claim 1, wherein the first area is formed on an inner portion of an outer circumferential surface of the second housing, and the second area is formed on an outer portion of the outer circumferential surface of the second housing.

7. The sound output device of claim 1, wherein the first area is made of a material having higher UVA transmissivity than the second area.

8. The sound output device of claim 1, wherein the first area is made of a material having higher UVC transmissivity than UVC transmissivity of the second area.

9. The sound output device of claim 1, wherein the first area is made of a material having higher infrared transmissivity than the second area.

10. The sound output device of claim 1, wherein the light emitting unit includes at least one light source configured to emit at least any one of UVA, UVB, UVC, and infrared rays.

11. The sound output device of claim 1, further comprising:
   a control unit disposed on the substrate and configured to control an operation of at least one of the light emitting unit and the sound output unit,
   wherein the control unit drives the light emitting unit for a predetermined time when a sound signal is received from a terminal.

12. The sound output device of claim 1, wherein the sound output unit amplifies a sound collected from the outside and outputs the amplified sound.

* * * * *